US00PP31678P2

(12) United States Plant Patent
Hansen

(10) Patent No.: US PP31,678 P2
(45) Date of Patent: Apr. 14, 2020

(54) ***KNIPHOFIA* PLANT NAMED 'LUCKY LEMONS'**

(50) Latin Name: ***Kniphofia* hybrid**
Varietal Denomination: Lucky Lemons

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,858

(22) Filed: Jan. 24, 2019

(51) Int. Cl.
*A01H 5/02* (2018.01)
*A01H 6/00* (2018.01)

(52) U.S. Cl.
USPC ..... Plt./443

(58) Field of Classification Search
USPC ..... Plt./443
CPC ..... A01H 6/00; A01H 5/02
See application file for complete search history.

*Primary Examiner* — Keith O. Robinson

(57) ABSTRACT

A new and distinct cultivar of Red Hot Poker plant named *Kniphofia* 'Lucky Lemons' with long, gracefully-arching, strap-like, keeled, glaucous, gray-green foliage and numerous spikes. Habit is densely growing, winter-hardy, tolerant of heat, deer and rabbits. Numerous scapes of green buds that lighten to pastel-yellow before opening to creamy-yellow flowers on tall scapes beginning in mid-July and repeating for five weeks. The new plant is useful for landscaping as a specimen, en masse, or as a long-lasting cut flower.

1 Drawing Sheet

Botanical classification: *Kniphofia* hybrid.
Variety denomination: 'Lucky Lemons'.

STATEMENT REGARDING PRIOR DISCLOSURES UNDER 37 CFR 1.77(B)(6)

The first public disclosure of the claimed plant, in the form of a photograph and brief description was on a website operated by Walters Gardens, Inc. on Feb. 1, 2018. After that, on Jun. 4, 2018 the claimed plant was sold by Walters Gardens, Inc., who obtained the plant and all information relating thereto, from the inventor. No plants of *Kniphofia* 'Lucky Lemons' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

The present invention relates to the new and distinct Red Hot Poker, *Kniphofia* 'Lucky Lemons' developed under the direction of the inventor at a wholesale perennial nursery in Zeeland, Mich., USA on Aug. 22, 2013 and harvested in the fall of 2013. The new plant was a single seedling selection resulting from a cross of 'Papaya Popsicle' U.S. Plant Pat. No. 22,915 as the female parent or seed parent and 'Sally's Comet' (not patented) as the male parent. The plant passed initial evaluation in the summer of 2015 and was subsequently given the breeder code 13-8-20 prior to naming. *Kniphofia* 'Lucky Lemons' has been successfully asexually propagated by division method since 2015 at the same wholesale perennial nursery in Zeeland, Mich. and subsequently by shoot tip tissue culture, and both methods have been found to be stable and produce identical plants that maintain the unique characteristics of the original plant through multiple generations.

SUMMARY OF THE PLANT

*Kniphofia* 'Lucky Lemons' differs from its parents as well as all other *Kniphofia* known to the applicant. The most similar known *Kniphofia* cultivars are: the female parent 'Papaya Popsicle', the male parent 'Sally's Comet' (not patented), 'Banana Popsicle' U.S. Plant Pat. No. 27,617, 'Pineapple Popsicle' U.S. Plant Pat. No. 22,969, 'Poco Yellow' U.S. Plant Pat. No. 27,616, 'Solar Flare' U.S. Plant patent application Ser. No. 16/350,525 and 'Flashpoint' U.S. Plant patent application Ser. No. 16/350,526. 'Papaya Popsicle' is slightly shorter in habit and scape height and more reddish in flower color and the new plant is more persistent in the Michigan winter landscape. 'Sally's Comet' is slightly shorter in flower scape and foliage height and the flower color is a slightly deep yellow. 'Banana Popsicle' is significantly shorter in habit and flower scapes, fewer flowers per stem and the flowers have less green and more yellow in the young buds and deeper gold in the flower color. 'Pineapple Popsicle' is shorter in habit with flower stems lower than the top of the leaves, the flowers are smaller and the tepal color fades to a lighter color with age. 'Poco Yellow' is much smaller in scape height, foliage height and overall habit and has a lighter yellow flower color with less green coloration in the young buds. 'Solar Flare' has a deeper yellow flower color and is slightly shorter in habit. 'Flashpoint' has a slightly taller habit, and the flower buds are more chartreuse and open more chartreuse-cream.

*Kniphofia* 'Lucky Lemons' differs from these above cultivars and all cultivars known to the inventor in that it has:

1. Gracefully arching, strap-like, keeled, gray-green foliage.

2. Rapidly growing, dense habit, winter-hardy, heat tolerant, rabbit and deer tolerant, large-sized clumps.
3. Numerous spikes of green buds that lighten to pastel-yellow before opening to creamy yellow flowers on tall stems;
4. Flowering in mid-July and repeating for five weeks in Michigan.

BRIEF DESCRIPTION OF THE DRAWINGS

The photographs of *Kniphofia* 'Lucky Lemons' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
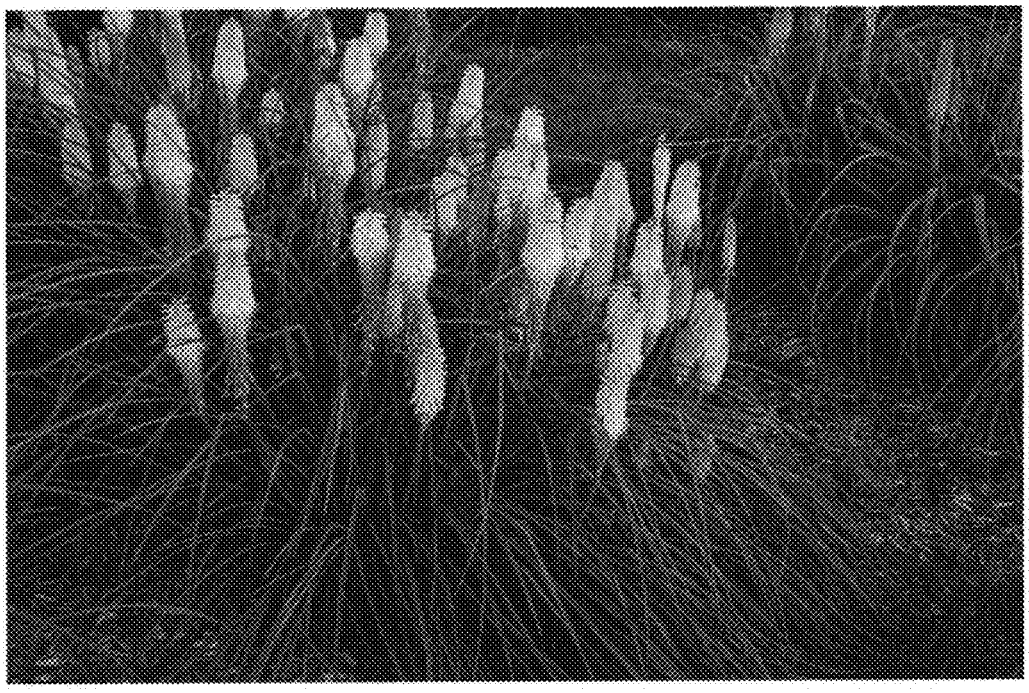
FIG. 1 shows the side-view habit of a five-year-old plant in midseason flowering.
Figure 2:
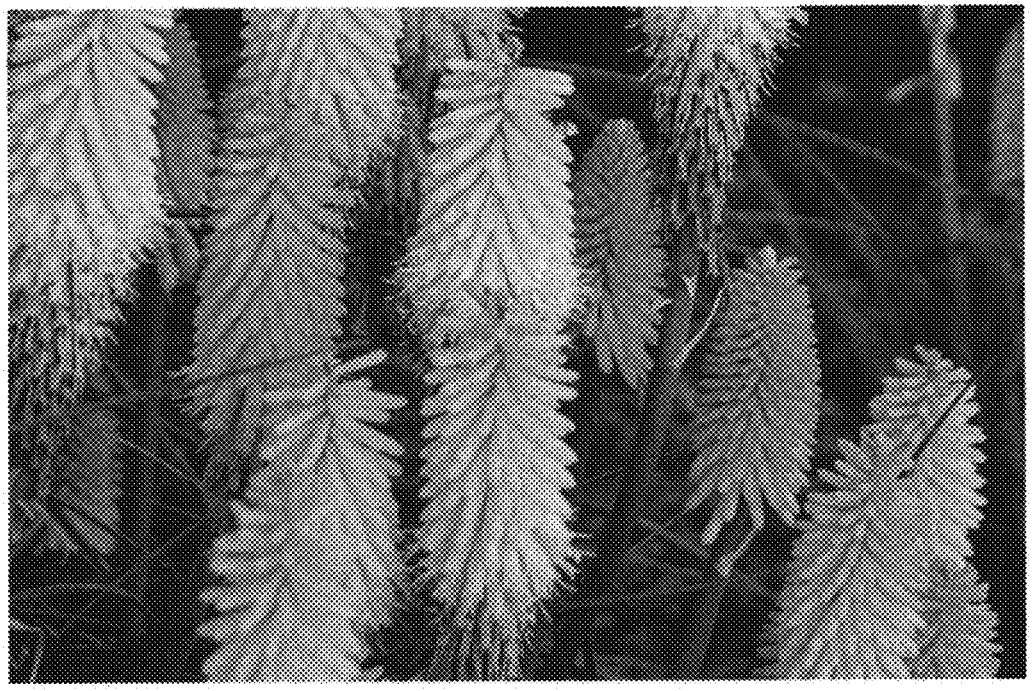
FIG. 2 shows a close-up of the flowers and buds.

The following descriptions and color references are based on the 2015 edition of The Royal Horticultural Society Colour Chart except where common dictionary terms are used. The new plant, *Kniphofia* 'Lucky Lemons', has not been observed under all possible environments. The phenotype may vary slightly with different environmental conditions, such as temperature, light, fertility, moisture and maturity levels, but without any change in the genotype. The following observations and size descriptions are of a five-year-old plant in a trial garden of a wholesale perennial nursery in Zeeland, Mich. under full sun with supplemental water and fertilizer as needed.

Botanical classification: *Kniphofia* hybrid;

Parentage: *Kniphofia* 'Papaya Popsicle' as the female or seed parent and the male or pollen parent is 'Sally' Comet';

Propagation method: By garden division of the rhizome and shoot tip tissue culture;

Growth rate: Vigorous, flowering in 3.5 liter containers in about 10 to 12 weeks from a tissue culture 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 220.0 cm across and about 90.0 cm tall; flowering to about 98.0 cm tall; about 60 peduncles per plant;

Leaves: Linear; keeled at base, triangular in distal half; arranged about 8 leaves per basal division; apex narrowly acute; base truncate, clasping; margin entire; no fragrance observed;

Leaf size: To about 116.0 cm long and 26.0 mm across at base, average about 84.0 cm long and 18.0 mm across at base;

Leaf color: Young base nearest RHS 145D both abaxial and adaxial, distally nearest RHS 146B both abaxial and adaxial; mature both surfaces between RHS 138A and RHS 146B;

Leaf venation: Parallel; color same as leaf abaxial and adaxial; color between RHS 138A and RHS 146B;

Stem: Acaulescent; rhizome about 18.0 mm across at base;

Inflorescence: In spike-like raceme; terete; about 250 flowers per stem; flowering portion to about 40.0 cm tall and about 6.0 cm across; lasting about three weeks; flower spacing less than 1.0 mm apart on raceme in distal region and about 2.5 cm in lowest flowers;

Peduncle: Terete; glabrous; glaucous; solid not fistulose; mostly erect; to about 98.0 cm long and 14.0 mm diameter; average 92.0 cm tall and 12.0 mm diameter;

Peduncle color: Between RHS 144A and RHS 146C;

Buds one day prior to opening: Ellipsoidal to tubular with swollen subacute apex and rounded base; glabrous; lustrous; about 23.0 mm long and about 3.0 mm diameter at base and 4.5 mm diameter at widest point near apex;

Bud attitude: Beginning outwardly and drooping as maturing toward anthesis;

Bud color: Abaxial dorsal portions nearest RHS 3B, nearest RHS 2D in ventral, with midribs nearest RHS 150C;

Flowers: Cylindrical forming tubular corolla; perfect; actinomorphic; individually open and effective about three to four days; to about 31.0 mm long to tip of exserted anthers and style and 7.0 mm wide at apex;

Corolla size: To about 23.0 mm long, fused in basal about 19.0 mm and divided in the distal 4.0 mm; face to about 7.0 mm tall and about 7.0 mm wide; tube about 3.5 mm diameter near base and about 5.5 mm near throat;

Flower attitude: Drooping;

Flower fragrance: None detected;

Flowering period: Individual racemes effective for about 3 weeks; beginning mid-July in Michigan for about five weeks;

Tepals: Six, in two identical sets of three; both sets with acute apices and fused in basal 19.0 mm forming tube; margin entire; glabrous and lustrous abaxial and adaxial; about 23.0 mm long and about 2.5 mm across just above fusion point;

Tepal color: Adaxial and abaxial nearest RHS 1D, adaxial midribs nearest RHS 150D, abaxial midribs nearest RHS 150C;

Androecium: Six; variable lengths, with filament lengths from 25.0 mm to 31.0 mm;

*Filaments*.—Six; exserted; cylindrical; glabrous; lustrous; from about 25.0 to 31.0 mm long and about 0.5 mm diameter; color between RHS 1C and RHS 1B.

*Anther*.—Slightly flattened ellipsoidal; flattened ventrally to dorsally; dorsifixed; longitudinal; about 2.5 mm long and 1.5 mm across and 1.0 mm thick; color nearest RHS 4A with occasional blush marks of nearest RHS 166B.

*Pollen*.—Abundant: color nearest RHS 13A.

Gynoecium: Single; about 31.0 mm long;

*Style*.—Cylindrical; glabrous; lustrous; about 28.5 mm long and 0.7 mm diameter: color nearest RHS 4D toward base nearest RHS 2C distally.

*Stigma*.—Flattened, round; about 0.5 mm across; color nearest RHS 6D.

*Ovary*.—Superior; globose; rounded apex, truncate base; about 2.5 mm long and 2.0 mm diameter; color nearest RHS N144D.

Pedicel: Terete; glabrous; stiff; slightly drooping; about 2.0 mm long and about 1.0 mm diameter;

Pedicel color: Nearest RHS 183B;

Bracts: Lanceolate; hyaline; at cauline nodes and subtending individual flowers; with acute apices and truncate base; to about 9.0 mm long and 4.0 mm across at base; decreasing distally; average about 5.0 mm long and 2.5 mm across; color blushed with nearest RHS 167D;

Fruit: Tri-valved loculicidal capsule; ellipsoidal; about 6.0 mm long and 4.0 mm across; glabrous; with rounded apex and rounded base; typically five to nine seeded; color upon maturity nearest RHS 200A;

Seed: Irregular with angular sides, acute apex and base; about 4.0 mm long and 2.5 mm across; color nearest RHS 200A;

Disease and pest resistance: 'Lucky Lemons' is slightly susceptible to rust. There are many genera of pathogenic rusts, but the specific identification of the slight rust found on the new plant has not been identified and is not known by the inventor. Resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of Red Hot Poker plant named *Kniphofia* 'Lucky Lemons' as herein described and illustrated.

* * * * *